US009020192B2

(12) United States Patent
Qu et al.

(10) Patent No.: US 9,020,192 B2
(45) Date of Patent: Apr. 28, 2015

(54) HUMAN SUBMENTAL PROFILE MEASUREMENT

(71) Applicant: Access Business Group International LLC, Ada, MI (US)

(72) Inventors: Di Qu, Ada, MI (US); Gopa Majmudar, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 61 days.

(21) Appl. No.: 13/799,900

(22) Filed: Mar. 13, 2013

(65) Prior Publication Data
US 2013/0272571 A1 Oct. 17, 2013

Related U.S. Application Data

(60) Provisional application No. 61/622,809, filed on Apr. 11, 2012.

(51) Int. Cl.
| *G06K 9/00* | (2006.01) |
|---|---|
| *G06K 9/62* | (2006.01) |
| *A61B 5/107* | (2006.01) |

(52) U.S. Cl.
CPC .......... *G06K 9/6201* (2013.01); *G06K 9/00281* (2013.01); *A61B 5/1077* (2013.01); *A61B 5/1079* (2013.01)

(58) Field of Classification Search
None
See application file for complete search history.

(56) References Cited

U.S. PATENT DOCUMENTS

| 4,335,427 | A | | 6/1982 | Hunt et al. | |
|---|---|---|---|---|---|
| 4,905,702 | A | | 3/1990 | Foss | |
| 5,148,477 | A | | 9/1992 | Neely et al. | |
| 5,659,625 | A | | 8/1997 | Marquardt | |
| 5,825,941 | A | * | 10/1998 | Linford et al. | 382/294 |
| 6,251,070 | B1 | | 6/2001 | Khazaka | |
| 6,301,370 | B1 | | 10/2001 | Steffens et al. | |
| 6,381,488 | B1 | | 4/2002 | Dickey et al. | |
| 6,671,391 | B1 | * | 12/2003 | Zhang et al. | 382/118 |
| 6,751,340 | B2 | * | 6/2004 | Prokoski | 382/118 |
| 6,785,410 | B2 | | 8/2004 | Vining et al. | |

(Continued)

FOREIGN PATENT DOCUMENTS

WO WO 01/78016 A1 10/2001

OTHER PUBLICATIONS

Gürlek et al., "Augmentation Mentoplasty with Diced High-Density Porous Polyethylene," Department of Plastic, Reconstructive, and Aesthetic Surgery, Inönü University, Medical Faculty, American Society of Plastic Surgeons, vol. 119, No. 2, Feb. 2007, pp. 684-691.

(Continued)

*Primary Examiner* — Tahmina Ansari
(74) *Attorney, Agent, or Firm* — Brinks Gilson & Lione

(57) ABSTRACT

An imaging system captures images of a human submental profile in a dimension controlled environment and utilizes image analysis algorithms for detecting submental changes. Instead of implementing a strict posture control of a subject, the imaging system allows the subject to freely move his/her head in an up-and-down direction and a high speed camera captures this movement through a series of images at varying head-to-shoulder angles. The image analysis algorithms may accurately compare before and after images at similar head-to-shoulder angles to identify changes in a human submental profile using a series of measurements and checkpoints.

21 Claims, 8 Drawing Sheets

(56) References Cited

U.S. PATENT DOCUMENTS

| | | | |
|---|---|---|---|
| 6,950,542 B2 | 9/2005 | Roesch et al. | |
| 7,006,657 B2 | 2/2006 | Bazin | |
| 7,027,618 B2 | 4/2006 | Trajkovic et al. | |
| 7,035,445 B2 | 4/2006 | Oosawa | |
| 7,133,496 B2* | 11/2006 | Wilson | 378/156 |
| 7,242,793 B2 | 7/2007 | Trobaugh et al. | |
| 7,499,574 B1 | 3/2009 | Yang et al. | |
| 7,587,078 B2 | 9/2009 | Zahniser et al. | |
| 7,616,797 B2 | 11/2009 | Bailey et al. | |
| 7,657,101 B2 | 2/2010 | Christiansen, II et al. | |
| 7,692,548 B2 | 4/2010 | Bonefas et al. | |
| 7,783,093 B2 | 8/2010 | Singh et al. | |
| 7,953,260 B2 | 5/2011 | Weinzweig et al. | |
| 7,972,266 B2 | 7/2011 | Gobeyn et al. | |
| 8,033,832 B1 | 10/2011 | Stefan et al. | |
| 8,068,675 B2 | 11/2011 | Christiansen, II et al. | |
| 8,107,695 B2 | 1/2012 | Wollenweber | |
| 8,126,231 B2 | 2/2012 | Sakaida | |
| 8,130,225 B2 | 3/2012 | Sullivan et al. | |
| 8,194,938 B2* | 6/2012 | Wechsler et al. | 382/118 |
| 8,711,178 B2* | 4/2014 | Cortes Provencio | 345/646 |
| 8,799,756 B2* | 8/2014 | Grosz et al. | 715/202 |
| 2002/0106114 A1* | 8/2002 | Yan et al. | 382/118 |
| 2002/0181752 A1 | 12/2002 | Wallo et al. | |
| 2003/0065523 A1 | 4/2003 | Pruche et al. | |
| 2004/0028263 A1 | 2/2004 | Sakamoto | |
| 2004/0184670 A1* | 9/2004 | Jarman et al. | 382/274 |
| 2005/0197542 A1 | 9/2005 | Bazin et al. | |
| 2006/0023228 A1* | 2/2006 | Geng | 356/601 |
| 2007/0047774 A1 | 3/2007 | Yukhin et al. | |
| 2007/0269089 A1 | 11/2007 | Sakaida | |
| 2007/0280556 A1 | 12/2007 | Mullick et al. | |
| 2008/0163880 A1* | 7/2008 | Garrell | 132/200 |
| 2008/0273745 A1 | 11/2008 | Bazin | |
| 2009/0179986 A1 | 7/2009 | Klett | |
| 2009/0231442 A1* | 9/2009 | Yonaha et al. | 348/207.2 |
| 2010/0284581 A1 | 11/2010 | Petit et al. | |
| 2010/0284582 A1 | 11/2010 | Petit | |
| 2011/0243406 A1 | 10/2011 | Chandler | |
| 2012/0059239 A1 | 3/2012 | Yamaguchi | |
| 2012/0223970 A1* | 9/2012 | Cortes Provencio | 345/646 |
| 2013/0272571 A1* | 10/2013 | Qu et al. | 382/103 |

OTHER PUBLICATIONS

Larrabee, Jr. et al., "Profile Analysis in Facial Plastic Surgery," Arch Otolaryngol., vol. 111, Oct. 1985, pp. 682-687.

Lin et al., "Three-Dimensional Imaging in Measuring Facial Aesthetic Outcomes," Laryngoscope 118; Oct. 2008, pp. 1733-1738.

Mattison, Richard C., MD, "Facial Video Image Processing: Standard Facial Image Capturing, Software Modification, Development of a Surgical Plan, and Comparison of Presurgical and Postsurgical Results," Annals of Plastic Surgery, vol. 29, No. 5, Nov. 1992, pp. 385-389.

Park et al., "Harmonized Profiloplasty Using Balanced Angular Profile Analysis," Aesthetic Plastic Surgery 28, 2004, pp. 89-97.

Pham et al., "Objective Facial Photograph Analysis Using Imaging Software," Facial Plastic Surgery Clinic North America 18, 2010, pp. 341-349.

Sattler et al., "Validated Assessment Scale for Neck Volume," American Society for Dermatalogic Surgery, Inc. 38:2, Part II, Feb. 2012, pp. 343-350.

Setaro et al., "Ptosis of Submental Skin, Objective Measurements and Effect of Age," Skin Research and Technology 2004: 10, pp. 251-256.

Swamy et al., "Pre- and Postoperative Portrait Photography: Standardized Photos for Various Procedures," Facial Plastic Surgery Clinic North America 18, 2010, pp. 245-252.

Thomas et al., "Analysis of Patient Response to Preoperative Computerized Video Imaging," Arch Otolaryngol., vol. 115, Jul. 1989, pp. 793-796.

Tollefson et al., "Computer Imaging Software for Profile Photograph Analysis," Arch Facial Plastic Surgery, vol. 9, Mar./Apr. 2007, pp. 113-119.

* cited by examiner

HUMAN SUBMENTAL PROFILE MEASUREMENT

PRIORITY

This application claims priority to U.S. Prov. App. No. 61/622,809, titled "HUMAN SUBMENTAL PROFILE MEASUREMENT," filed on Apr. 11, 2012, the entire disclosure of which is hereby incorporated by reference.

BACKGROUND

Measuring a human submental profile may be difficult due to human error in the imaging process. The human submental may be defined as anatomy situated beneath the chin or under the edge of the lower jaw, such as the neck area. After cosmetic surgery or other rejuvenation techniques it may be useful to have a quantitative measure of the resulting change. Accordingly, surgery or techniques applied to different patients can be quantitatively compared for a determination of respective effectiveness. For example, a procedure to change the shape of one's neck may include a visible change in the neck line. Three-dimensional imaging techniques may illustrate the differences, but are limited by a high expense and advanced computing techniques required to process the three-dimensional data. Further, photographic comparisons require that the subject have the same posture and positioning for the before and after pictures. Slight difference in head-to-shoulder angle may affect the comparison and prevent an accurate determination of submental changes.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

DETAILED DESCRIPTION

By way of introduction, the disclosed embodiments relate to detecting submental profile changes. Qualitative analyses of submental measurements detected errors from the difference in a head-to-shoulder angle when the subject's image is taken at different times (e.g. before and after a procedure). To better control this source of error, the proposed imaging system allows the subject to freely move his/her head in an up-and-down direction. A high speed camera for capturing images of a human submental profile in a dimension controlled environment with image analysis algorithms may be used for detecting submental changes. Human error may be reduced when measuring a human submental profile by limiting head movement using a dimension controlled environment. The image analysis algorithms may accurately identify changes in a human submental profile using a series of measurements and checkpoints to account for movement or shifting of the head during image acquisition. In particular, the image analysis system allows for the subject's head to move freely up and down because the position of head to shoulder is captured in a dynamic fashion by a series of images. In particular, a high speed camera may take multiple images of a subject while the subject raises/lowers her chin (i.e. looks up and down). Through image analysis, the head to shoulder angles can be calculated for each individual frame and from the series of images taken before and after treatment, exact subject posture can be selected at a specified angle. The design of the image capturing booth may improve the problem of proper subject positioning by controlling or limiting subject movement.

Figure 1:
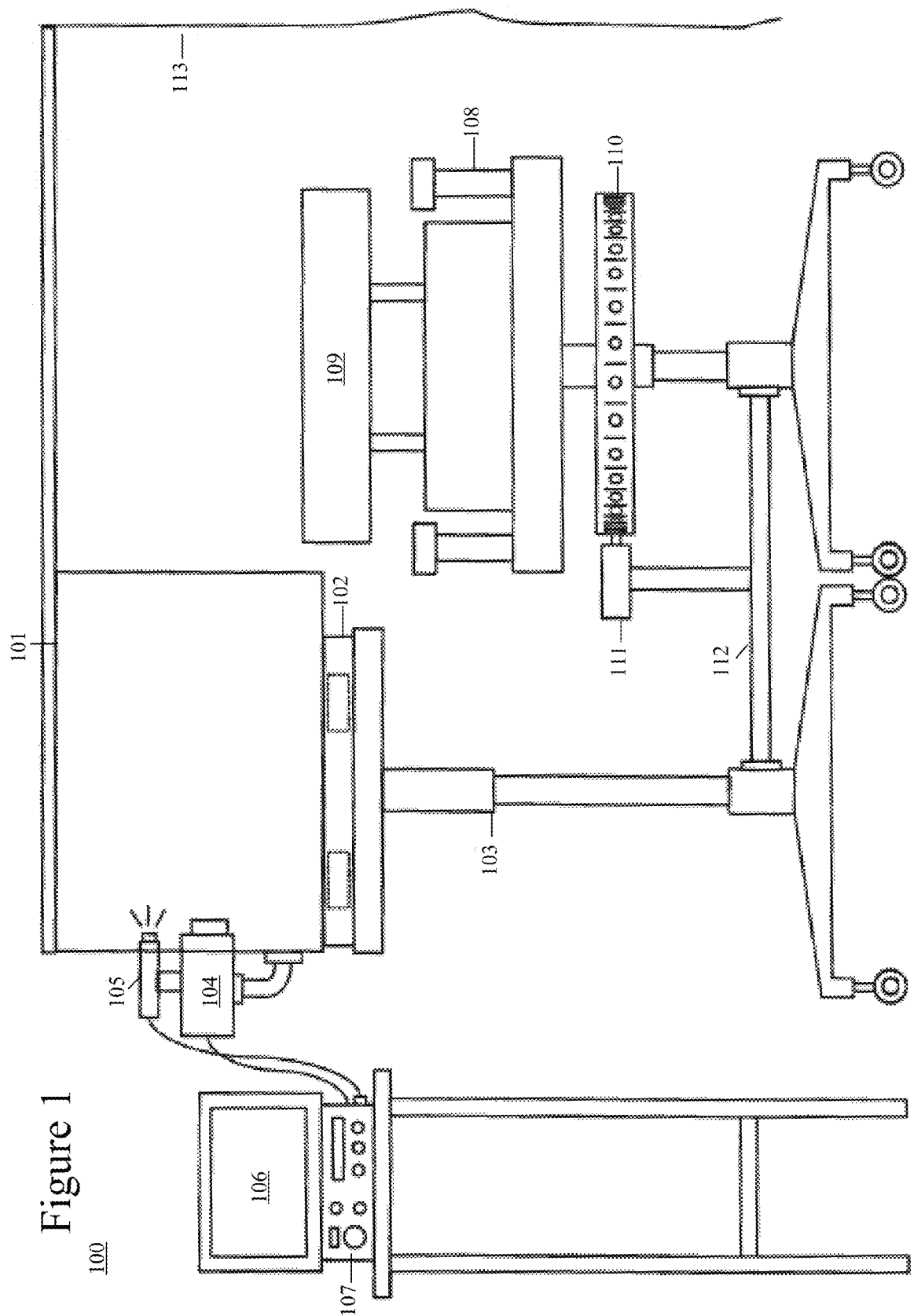
FIG. 1 illustrates an imaging system.

FIG. 1 illustrates an imaging system 100. The imaging system 100 may also be referred to as a dimension control mechanism in which images are taken of a subject or target. In one embodiment as described below, the subject is a human and the image acquisition is of the human's face in a profile view. The imaging system 100 may include a booth 101 for acquiring profile images in a consistent or constant environment. The booth 101 includes a horizontal slider 102 along with a vertically adjustable stand 103 for moving the booth relative to the subject. The booth 101 further includes a camera 104 along with a light 105 for acquiring images of the subject. The camera 104 may be a high-speed camera and may include any digital still camera that takes multiple images with at least three frames per second. Alternatively, the camera 104 may include any digital video camera which captures the movement of a subject's head and the resulting video can then be converted to individual digital frames to achieve the same analysis. Since the imaging system 100 performs "before" and "after" profile images, the imaging system 100 and the booth 101 should be consistent for both the "before" image acquisition and the "after" image acquisition. As described below, the image analysis algorithms attempt to account for differences between the different sets of images. For example, if the booth 101 is closer to the subject in one of the sets of images, then the resulting comparison would be flawed if the image analysis failed to account for those differences.

The images taken by the camera 104 are provided to a camera control panel 107 connected with an image display monitor 106. The image display monitor 106 displays the images for a user of the imaging system 100. The image display monitor 106 may be a liquid crystal display (LCD), an organic light emitting diode (OLED), a flat panel display, a solid state display, a cathode ray tube (CRT), a projector, a printer or other now known or later developed display device for outputting determined information. The image display monitor 106 may function as an interface for the user/administrator to modify the algorithms used for image analysis and/or to identify tracking points or measurements on the images that are used for the comparisons.

The user of the imaging system 100 may control the camera 104 utilizing the camera control panel 107. In alternative embodiments, the images are stored at the camera control panel 107 or with another storage device. In one example, the camera 104 may store the images to a digital storage medium, such as a hard drive, solid-state drive, flash memory, secure digital (SD) card, or other memory device. Alternatively, a computing device or storage medium may be connected with the camera 104 and/or the camera control panel 107 for storing the images, such as the image analyzer that is described below with respect to FIGS. 2 and 3.

The subject may be controlled or put into a set position utilizing a chair 108. The chair 18 may include a vertically adjustable chair back 109 for positioning the subject adjacent to the booth 101 for optimal image acquisition. A circular scale 110 coupled with the chair 108 may be used for turning the chair 108. A spring latch 111 and a connector 112 may be used for connecting the booth 101 with the chair 108. In particular, the connector 112 ensures that the distance from the camera 104 to the subject is consistent for both the "before" and "after" sets of images. A curtain 113 is behind the subject so that the image taken by the camera 104 has a consistent background. In one embodiment, the curtain 113 is black and the images taken are of a human profile with a black background. The color of the curtain 113 may be varied to distinguish the face in the images.

The imaging system 100 in FIG. 1 may be used for controlling or regulating the positioning of a subject for both before and after images. In particular, the booth 101 and positioning of the chair 109 can improve consistency in the images that are taken at different times. In one embodiment, there may be additional dimensions or features that can be used with the imaging system 100 to achieve consistency in positioning of the subject. The following illustrate features that may be utilized in one or more embodiments. First, the image capturing booth 101 may improve the control of the profile. In one embodiment, the booth 101 is 22×22 inches in height and width, and 24 inches deep to allow a proper view of subject's head and submental area. Second, the horizontal location of the camera 104 may be controlled by the horizontal sliding fixture 102. Third, the vertical position of the high speed camera may be controlled by a vertical adjustable stand 103. Fourth, the distance of subject relative to the camera lens is controlled by a connector 112 fixing the chair 109 and the adjustable stand 103 together at a constant distance. Fifth, the height of subject relative to the booth is controlled by a vertically adjustable chair 109. Sixth, the subject's shoulder position may be controlled by asking the subject to lean his/her shoulders flat against the back of chair. Accordingly, the back of chair should be flush with the height of subject's shoulder, so the back of chair 109 may include an adjustable top section. Seventh, the direction in which the subject faces is controlled by a frame on the chair with a circular scale 110. A spring latch 111 may be mounted on the connector between the stand 103 and the chair 109 which is used to control the direction that the chair 109 (and consequently the subject) faces.

Herein, the phrase "coupled with" is defined to mean directly connected to or indirectly connected through one or more intermediate components. Such intermediate components may include both hardware and software based components. Variations in the arrangement and type of the components may be made without departing from the spirit or scope of the claims as set forth herein. Additional, different or fewer components may be provided.

Figure 2:
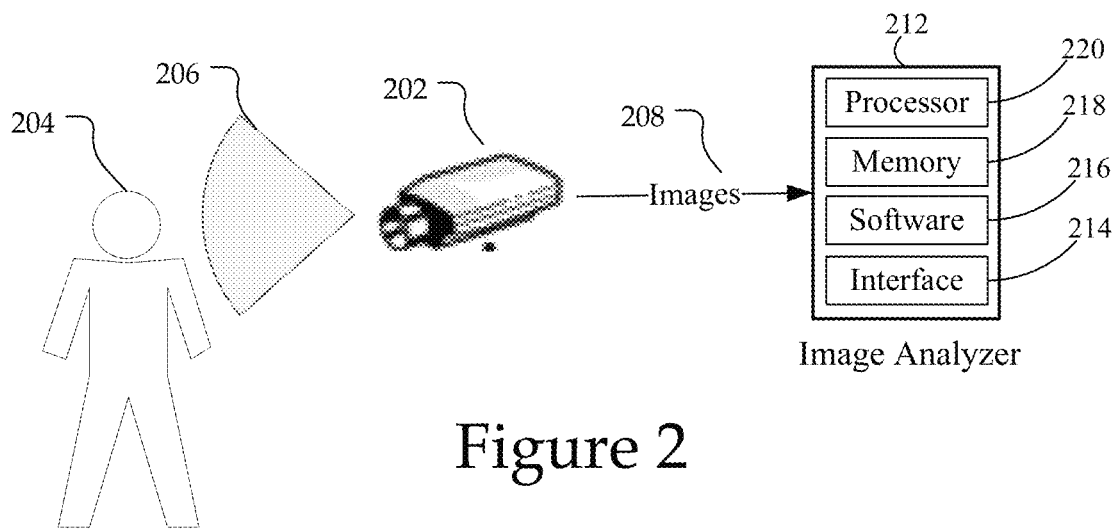
FIG. 2 illustrates an alternative embodiment of the imaging system.

FIG. 2 illustrates an alternative embodiment of the imaging system 100. In particular, FIG. 2 illustrates a camera 202, which takes an image 206 of a subject 204. The camera 202 may be the same or different from the camera 104 from FIG. 1 and references to the camera 104 and/or the camera 202 may be interchangeable. The subject 204 may be a human and specifically may be a profile image of the human head or face, such as those shown in FIGS. 5-6 and 8-9. The subject 204 may refer to the subject of the image, which in one embodiment, is a profile view of a human head. The subject 204 may also be referred to as a target. In alternative embodiments, some of the features described herein may be applied to different types of subjects and different angles of the subject (i.e. other than a profile image); however, the following disclosure describes the embodiment of image acquisition of a profile of a human face. The images 208 are taken or acquired by the camera 202 and submitted to an image analyzer 212. As described below, one or more algorithms from the image analyzer 212 may be used to determine any changes in a submental with "before" and "after" sets of profile images.

The image analyzer 212 may be used for identifying changes to a submental. The image analyzer 212 may be a computing device for receiving image data and running algorithms/analysis on that image data to determine changes to a human submental. As shown, the image analyzer 212 may be a part of the camera control panel 107 and/or the image display monitor 106. As shown, the camera 202 provides the image data; however, the image analyzer 212 may receive image data from other sources for analysis. The image analyzer is further described with respect to FIG. 3.

The image analyzer 212 may include a processor 220, a memory 218, software 216 and an interface 214. The interface 214 may be a user input device or a display. The interface 214 may include a keyboard, keypad or a cursor control device, such as a mouse, or a joystick, touch screen display, remote control or any other device operative to allow a user or administrator to interact with the image analyzer 212. The interface 214 may communicate with the camera 202, the camera control panel 107, and/or the image display monitor 106. The interface 214 may include a user interface configured to allow a user and/or an administrator to interact with any of the components of the image analyzer 212. For example, the administrator and/or user may be able to modify the algorithms that are part of the image analysis or generate the tracking points and measurements that are used for the algorithms as further described below. The interface 214 may include a display (e.g. the image display monitor 106) coupled with the processor 220 and configured to display the received images and/or results from the comparison of images as calculated by the processor 220.

The processor 220 in the image analyzer 212 may include a central processing unit (CPU), a graphics processing unit (GPU), a digital signal processor (DSP) or other type of processing device. The processor 220 may be a component in any one of a variety of systems. For example, the processor 220 may be part of a standard personal computer or a workstation. The processor 220 may be one or more general processors, digital signal processors, application specific integrated circuits, field programmable gate arrays, servers, networks, digital circuits, analog circuits, combinations thereof, or other now known or later developed devices for analyzing and processing data. The processor 220 may operate in conjunction with a software program, such as code generated manually (i.e., programmed).

The processor 220 may be coupled with the memory 218, or the memory 218 may be a separate component. The software 216 may be stored in the memory 218. The memory 218 may include, but is not limited to, computer readable storage media such as various types of volatile and non-volatile storage media, including random access memory, read-only memory, programmable read-only memory, electrically programmable read-only memory, electrically erasable read-only memory, flash memory, magnetic tape or disk, optical media and the like. The memory 218 may include a random access memory for the processor 220. Alternatively, the memory 218 may be separate from the processor 220, such as a cache memory of a processor, the system memory, or other memory. The memory 218 may be an external storage device or database for storing recorded tracking data, or an analysis of the data. Examples include a hard drive, compact disc ("CD"), digital video disc ("DVD"), memory card, memory stick, floppy disc, universal serial bus ("USB") memory device, or any other device operative to store data. The memory 218 is operable to store instructions executable by the processor 220.

The functions, acts or tasks illustrated in the figures or described herein may be performed by the programmed processor executing the instructions stored in the memory 218. The functions, acts or tasks are independent of the particular type of instruction set, storage media, processor or processing strategy and may be performed by software, hardware, integrated circuits, firm-ware, micro-code and the like, operating alone or in combination. Likewise, processing strategies may include multiprocessing, multitasking, parallel processing and the like. The processor 220 is configured to execute the software 216.

The present disclosure contemplates a computer-readable medium that includes instructions or receives and executes instructions responsive to a propagated signal, so that a device connected to a network can communicate voice, video, audio, images or any other data over a network. The interface 214 may be used to provide the instructions over the network via a communication port. The communication port may be created in software or may be a physical connection in hardware. The communication port may be configured to connect with a network, external media, display, or any other components in system 200, or combinations thereof. The connection with the network may be a physical connection, such as a wired Ethernet connection or may be established wirelessly as discussed below. Likewise, the connections with other components of the imaging system may be physical connections or may be established wirelessly.

Any of the components in the imaging system may be coupled with one another through a network. The image analyzer 212 may be coupled with other devices through a network to enable communication of data between the devices including wired networks, wireless networks, or combinations thereof. For example, the image analyzer 212 may provide the received images, the algorithm calculations, and/or the results of a comparison of images over a network. The wireless network may be a cellular telephone network, a network operating according to a standardized protocol such as IEEE 802.11, 802.16, 802.20, published by the Institute of Electrical and Electronics Engineers, Inc., or WiMax network. Further, the network(s) may be a public network, such as the Internet, a private network, such as an intranet, or combinations thereof, and may utilize a variety of networking protocols now available or later developed including, but not limited to TCP/IP based networking protocols. The network (s) may include one or more of a local area network (LAN), a wide area network (WAN), a direct connection such as through a Universal Serial Bus (USB) port, and the like, and may include the set of interconnected networks that make up the Internet. The network(s) may include any communication method or employ any form of machine-readable media for communicating information from one device to another.

Figure 3:
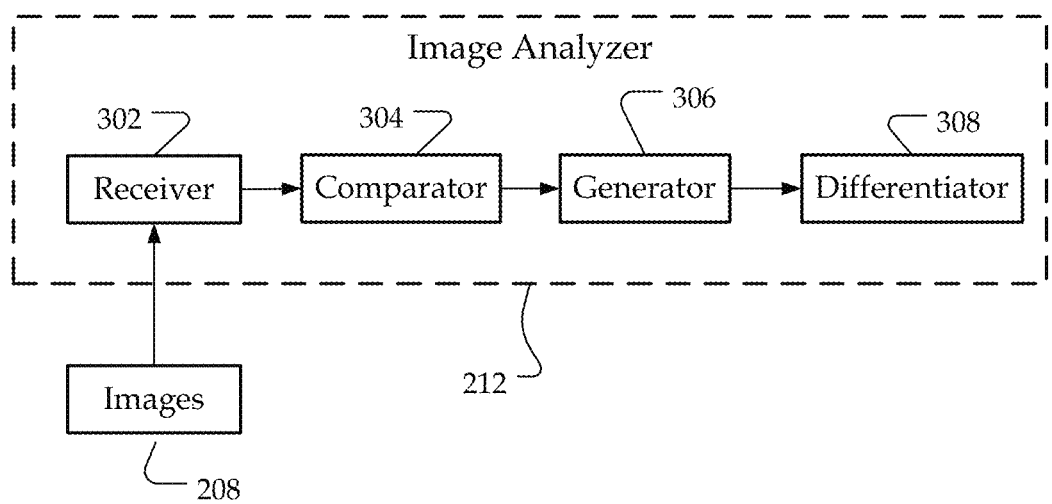
FIG. 3 illustrates one embodiment of an image analyzer.

FIG. 3 illustrates one embodiment of the image analyzer 212. A receiver 302 may receive the images 208. In one embodiment, the images 208 are received from a camera. In other embodiments, the images are received from another storage medium. The receiver 302 provides the images to a comparator 304 for comparing pictures from a "before" state and an "after" state. There may be a set of images from the "before" state with the head tilted at different angles and a set of images from the "after" state with the head tilted those angles that are compared. As described, the subject may slowly tilt their head forward or backward as multiple images are acquired from a camera. For example, the camera may be high-speed and may take 30 images per second. The higher speed the camera, the less chance of error in comparing images from the before and after sets that are at the same angle.

The generator 306 then determines the area of the submental area for the subject for both the before and after images. In particular, the generator 306 may establish tracking points and measurement points for analyzing the submental area using one or more algorithms as described with respect to FIGS. 4-9. In one embodiment, the generator 306 may calculate the area for the submental area before the comparator 304 compares those areas for before and after images at the same angle. In other words, the generator 306 performs the calculations for the submental area and then the comparator 304 sorts the images based on the same angles.

The differentiator 308 calculates the differences between the after and the before state. In one embodiment, there are multiple calculations for multiple head angles. For example, there may be both a before and after picture at an identical set of ten angles and the submental difference is calculated for each of those ten.

Figure 4:
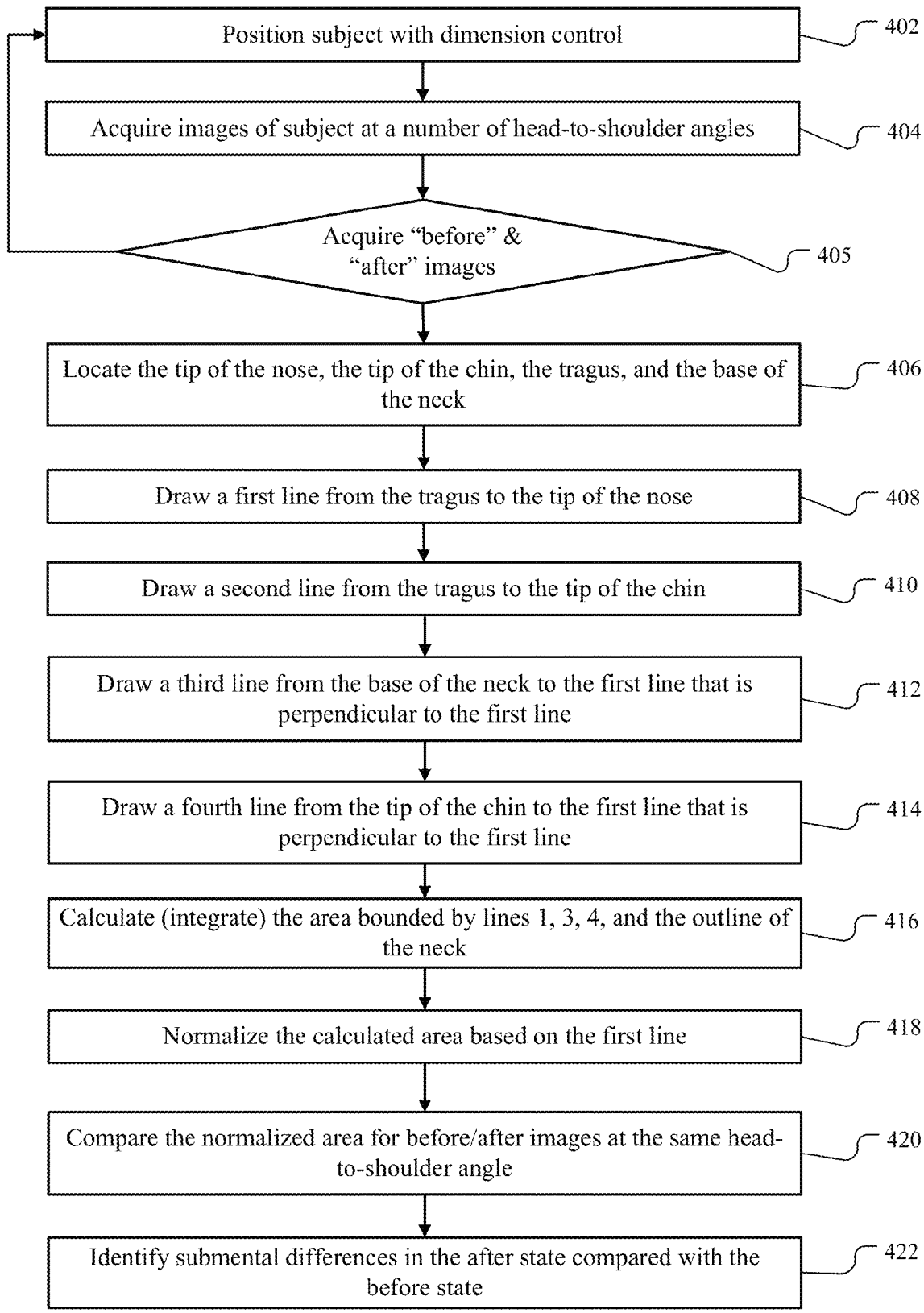
FIG. 4 is a flow chart illustrating image analysis.

FIG. 4 is a flow chart illustrating image analysis. In block 402, the subject is positioned within the imaging system 100. In particular, the human subject 204 may be seated in a chair 109 across from a camera 104. As described with respect to FIG. 1, the subject may be seated for a series of profile images of the subject's head, while the subject raises/lowers his/her head as in block 404. By raising his/her head, a series of images are acquired at a variety of head-to-shoulder angles. By collecting images at different head-to-shoulder angles, it may be easier to compare images from earlier/later times by matching the head-to-shoulder angle of images from different times. In one embodiment, the subject may be instructed to start with his/her chin in the lowest position (i.e. subject attempts to touch their chin to the base of their neck or chest) and raise their chin to the highest point (i.e. looking straight up) while multiple images are acquired.

Figure 5:
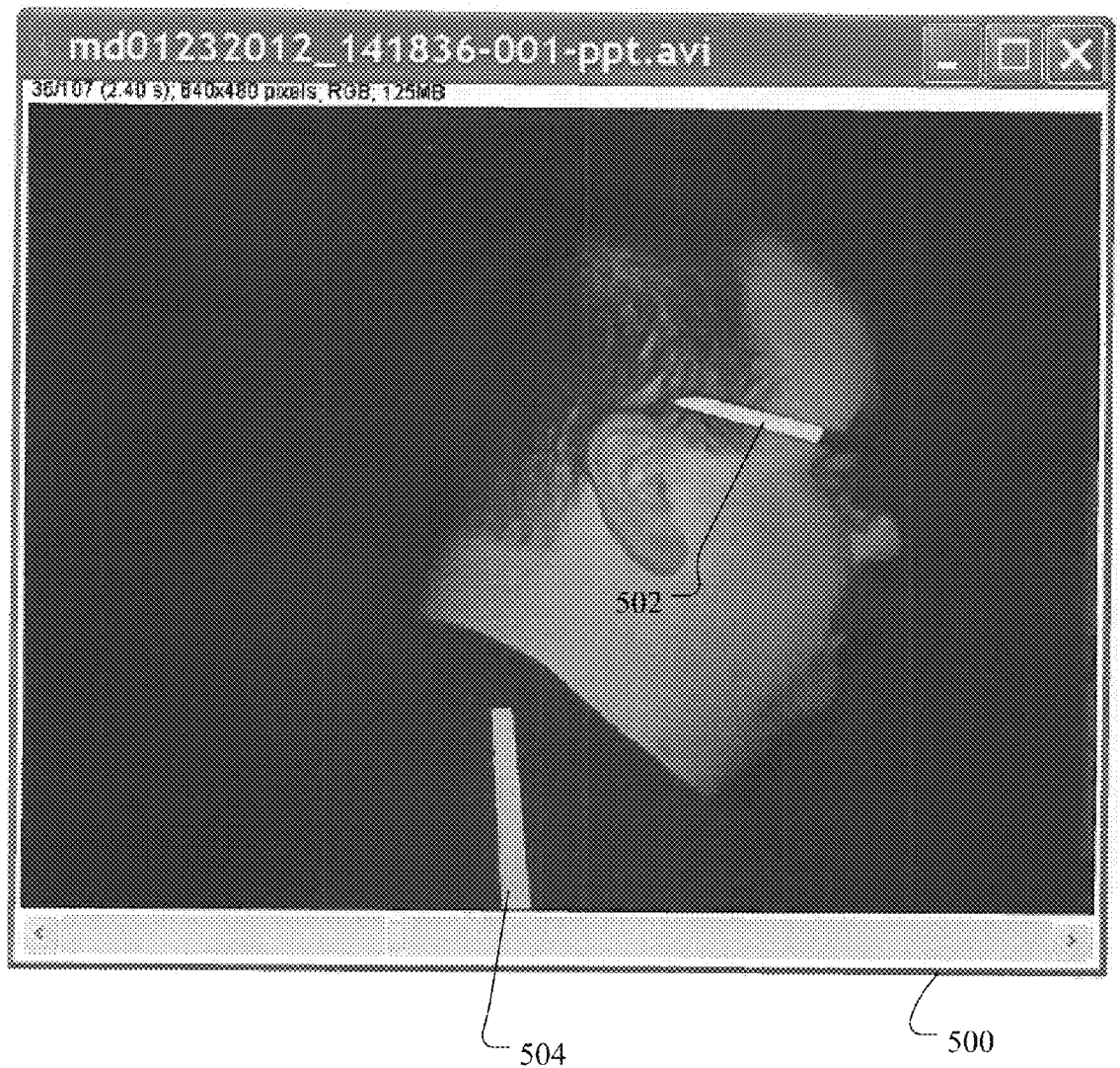
FIG. 5 is an exemplary profile image.

FIG. 5 is an exemplary profile image 500. In one embodiment, a subject may utilize glasses with a horizontal identifier 502 with a reflective or colored ear portion along with a vertical identifier 504, which may be part of or attached to a subject's shirt. In one embodiment, a special shirt or jacket may be worn that includes the vertical identifier 504. Rather than glasses, the horizontal identifier 502 may be otherwise attached to the subject's head, such as with a hat or as a sticker for the subject's face. The purpose of the horizontal identifier 502 and the vertical identifier 504 is for determining a head-to-shoulder angle. As long as the horizontal identifier 502 and the vertical identifier 504 are utilized consistently in the before and after series of pictures, the imaging analysis can compare images at the same angles. The camera 104 may take a series of images (e.g. 30 images per second) as the subject moves their head up or down. The movement results in a constant change in the angle between the horizontal identifier 502 and the vertical identifier 504.

Figure 6:
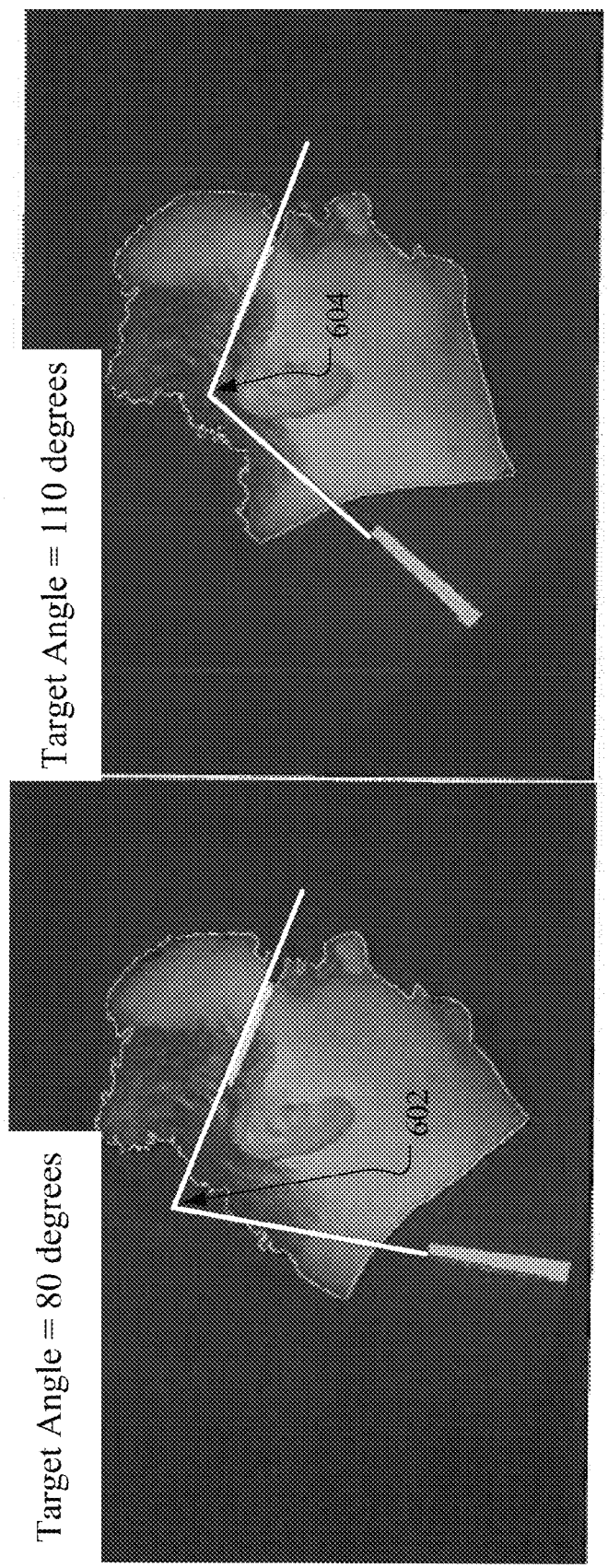
FIG. 6 is exemplary profile images at different angles.

FIG. 6 illustrates exemplary profile images at different angles. In particular, FIG. 6 illustrates two images (compare profile image 500 of FIG. 5) taken at different angles. In the first image, the angle 602 between the horizontal identifier 502 and the vertical identifier 504 is 80 degrees. In the second image, the angle 604 between the horizontal identifier 502 and the vertical identifier 504 is 110 degrees. In other words, the subject in the second image is looking up more than in the second image. Although not shown, the profile image of the head may be rotated for easier comparison. In one embodiment, a vertical line between the tip of the nose and the tangent of the forehead may be used as a reference line that is reoriented to be vertical. Accordingly, in FIG. 6, the first and second images shown are rotated such that the tip of the nose and the tangent of the forehead are vertical in both images.

Figure 7:
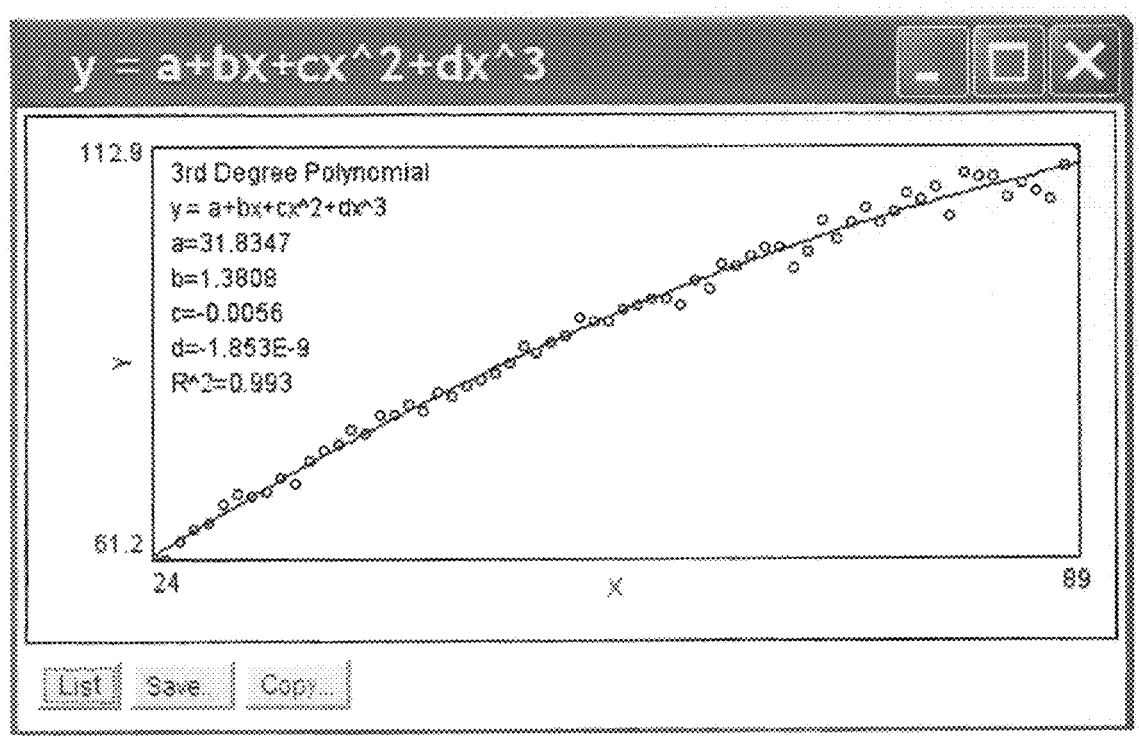
FIG. 7 illustrates the correspondence of the angles of profile images as the head is moved.

FIG. 7 illustrates the correspondence of the angles of profile images as the head is moved. In one embodiment, the series of images may include a video clip taken by the high speed camera, such as the camera 104. In one example, there may be 107 individual images/frames as a stack in avi format that are shown in FIG. 7. Using image analysis, those individual images may be separated from the stack and the head-to-shoulder angle is determined for each individual image. The result of this determination is the chart in FIG. 7 that correlates the frame number and the head-to-shoulder angle of each frame.

Referring back to FIG. 4 and as discussed above, there may be both before and after images that are taken in block 405. The before images may be a baseline taken to measure the effects of a subsequent surgery, operation, or other treatment. The after images can be compared with the before images to quantitatively measure the effects of the surgery, operation, or other treatment. For both the before and after images, there may be a number of images taken (e.g. 30 images per second) as the subject moves his/her head from a facing-down position to a facing-up position. Although, not described, the calculation of the area of the submental described with respect to FIGS. 406-418 may occur after the before images are acquired, but before the after images are acquired. Then the same calculations may be performed for the after images. In other words, block 405 may occur before block 420 such that the calculations are performed after acquiring the images for that state (before and after) rather than waiting for both states to be completed. In block 406, various reference locations or tracking points are identified for making certain measurements. The reference locations are used for establishing measurements or lines by which a submental area can be calculated and compared. In one embodiment, the area may include a portion of the face in addition to the submental area.

Figure 8:
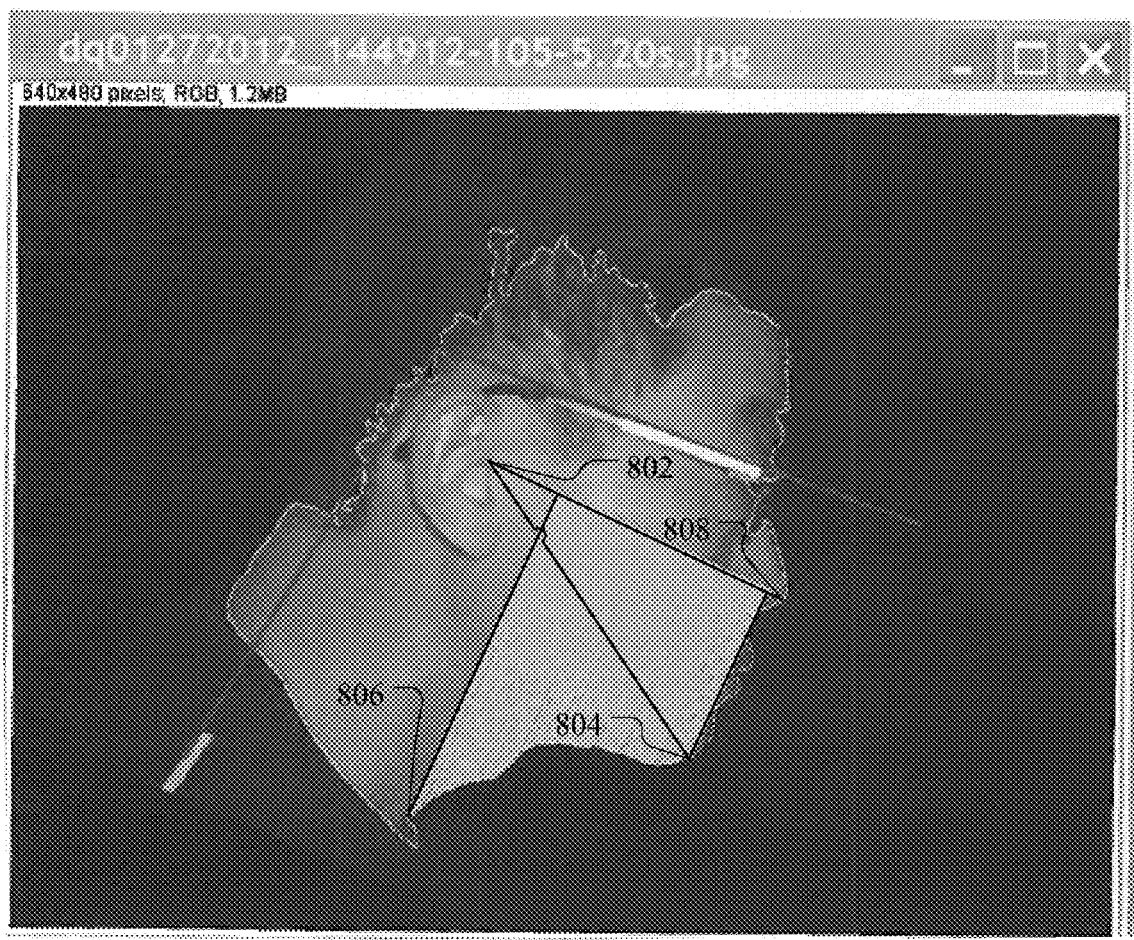
FIG. 8 illustrates a calculation of a first submental area.

FIG. 8 illustrates a calculation of a first submental area. In particular, the reference locations and connecting lines are shown. The tragus 802 is a point near the tip of the ear. In one embodiment, a user/administrator of the image analysis system manually identifies the tragus. Alternatively, the tragus 802 may be automatically identified based on the other features of the ear. The tip of the chin 804 may be identified manually or through image analysis. In one embodiment, the tip of the chin 804 may be at the point in which a line is perpendicular with the surface of the chin and connects with the tragus 802. The base of the neck 806 may include the point at which the neck reaches the chest/shoulder region. In one embodiment, a user/administrator of the image analysis system manually identifies the base of the neck 806. Alternatively, the base of the neck 806 may be automatically identified based on the other features around the base of the neck. The tip of the nose 808 may be identified manually or through image analysis. In one embodiment, the tip of the nose 808 may be at the point in which a line is perpendicular with the surface of the nose and connects with the tragus 802. The tip of the chin 804 and tip of the nose 808 are both points at which the tangent line from the curvature of the chin/nose respectively is normal at that point.

Figure 9:
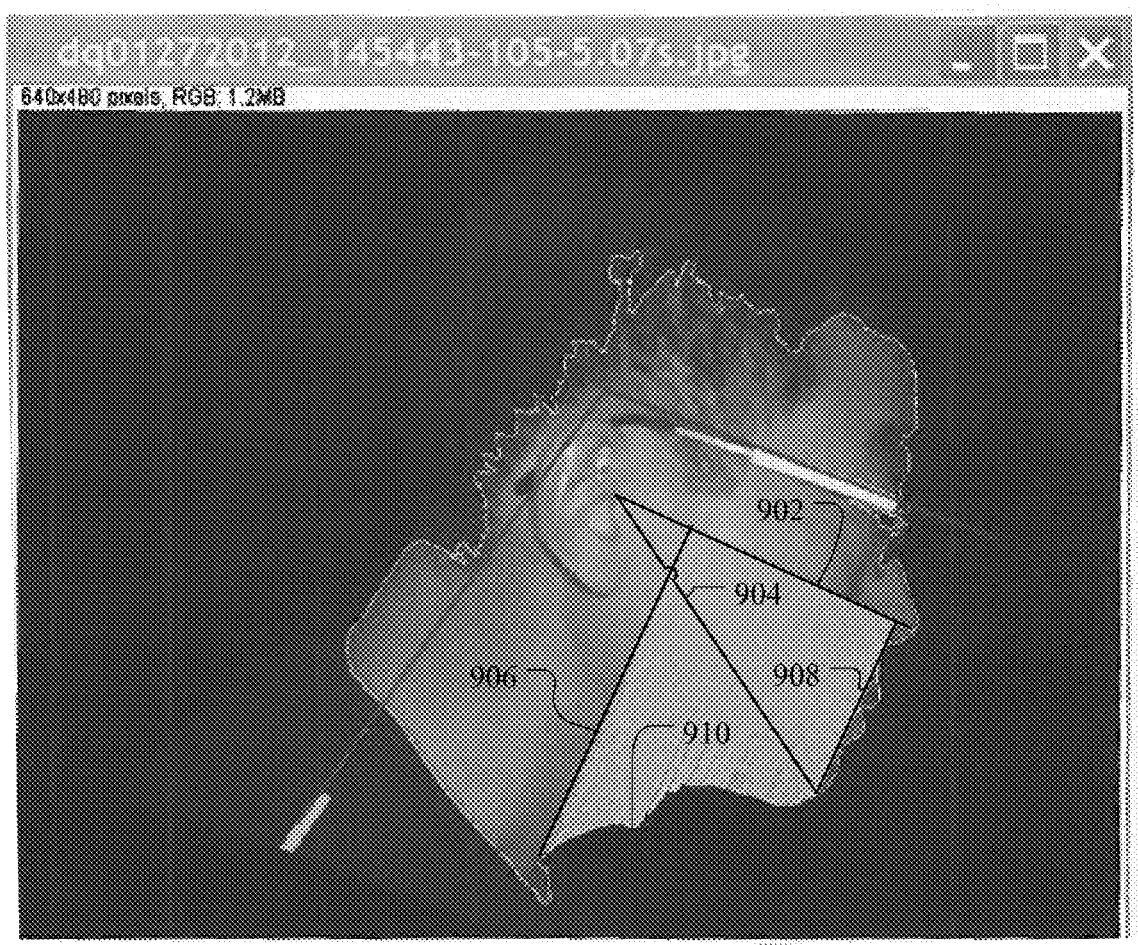
FIG. 9 illustrates a calculation of a second submental area.

There may be a number of lines used for measuring the submental that are generated based on the identified reference points in FIG. 8. Indeed, FIG. 8 illustrates those exemplary lines (unlabeled), which are further described with respect to FIG. 9. FIG. 9 illustrates a calculation of a second submental area. Referring back to FIG. 4 while referencing the lines shown in FIG. 9, in block 408, a first line 902 connects the tragus 802 and the tip of the nose 808. In block 410, a second line 904 connects the tragus 802 and the tip of the chin 804. In block 412, a third line 906 connects the base of the neck 806 to the first line 902 at the intersecting location where the third line 906 is perpendicular to the first line 902. In block 414, a fourth line 908 connects the tip of the chin 804 to the first line 902 at the intersecting location here the fourth line 908 is perpendicular to the first line 902.

Utilizing the lines identified in FIG. 9 an area can be calculated and normalized to correct against possible variations (e.g. the subject is slightly farther away or slightly closer to the camera). In block 416, the area bounded by the first line 902, the third line 906, the fourth line 908, and the outline of the neck between the base of the neck and the tip of the chin is calculated. This calculation may be an integration of the area or a summation of the pixels. In block 418, the calculated area is normalized based on the first line 902. In particular, the area calculated in block 416 may be normalized by dividing by the length of the first line 902. In block 420, the normalized areas for images from the before and after state are compared for the same head-to-shoulder angles. For example, a before image with a head-to-shoulder angle of 80 degrees will have its normalized area compared with the normalized area from an after image with a head-to-shoulder angle of 80 degrees. Given that the before and after image sets may include a number of images, this comparison may be made over a large sample size. Accordingly, in block 422, the submental differences in the after state are compared with the before state.

FIG. 9 illustrates a submental anomaly 910 that is detected using this image analysis. In particular, the anomaly 910 is a bandage on the subject and comparisons of the before images (without the bandage) and the after images (with the bandage) indicate that the submental has changed. In one embodiment, a cosmetic procedure may reduce the submental of a subject (e.g. remove fatty tissue or excess skin) and the image analysis described herein may be used to quantify the efficacy of such a procedure.

As described, FIG. 9 illustrates components or features of an image analysis algorithm performed by the image analyzer 212. The images may be obtained using an imaging system, such as the imaging system 100 shown in FIG. 1.

The system and process described above may be encoded in a signal bearing medium, a computer readable medium such as a memory, programmed within a device such as one or more integrated circuits, one or more processors or processed by a controller or a computer. That data may be analyzed in a computer system and used to generate a spectrum. If the methods are performed by software, the software may reside in a memory resident to or interfaced to a storage device, synchronizer, a communication interface, or non-volatile or volatile memory in communication with a transmitter. A circuit or electronic device designed to send data to another location. The memory may include an ordered listing of executable instructions for implementing logical functions. A logical function or any system element described may be implemented through optic circuitry, digital circuitry, through source code, through analog circuitry, through an analog source such as an analog electrical, audio, or video signal or a combination. The software may be embodied in any computer-readable or signal-bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine readable medium," "propagated-signal" medium, and/or "signal-bearing medium" may comprise any device that includes stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A method for identifying a change in a profile comprising:
   receiving a plurality of profile images at different head angles caused by vertical tilting of a chin for the profile images, wherein there are at least two sets profile images with the different head angles, a first set comprises before images and a second set comprises after images;
   determining an angle for each of the profile images;
   matching one of the before images with one of the after images based on the determined angle, wherein the matching comprises identifying multiple pairs of before and after images at different angles;
   calculating an area of the profile, including a submental area, for both of the matched before and after images for at least one of the pairs; and
   identifying changes in the matched after image when compared with the matching before image.

2. The method of claim 1 wherein the calculating the area further comprises:
   identifying a tip of a tragus, a tip of a nose, a tip of a chin, and a base of a neck for each of the before and after images for a matched pair of images;
   calculating an area bounded by at least a portion of the identified tip of the tragus, tip of the nose, tip of the chin, and base of the neck.

3. The method of claim 2 wherein the tip of the nose is identified by finding a tangent line from the nose that is perpendicular to a line through the tip of the tragus.

4. The method of claim 3 wherein the tip of the chin is identified by finding a tangent line from the chin that is perpendicular to a line through the tip of the tragus.

5. The method of claim 4 wherein the tangent line from the nose that is normal to the tip of the tragus comprises a first reference line and the tangent line from the chin that is normal to the tip of the tragus comprises a second line, further wherein the calculating the area further comprises:
   identifying a third reference line from the base of the neck that is perpendicular to the first reference line;
   identifying a fourth reference line from the tip of the chin that is perpendicular to the first reference line; and
   calculating an area bounded by the third reference line, the first reference line, the fourth reference line, and the neck.

6. The method of claim 5 further comprising:
   normalizing the calculated areas of the profile for both of the matched before and after images, wherein the normalizing comprises dividing the calculated area by a length of the first reference line.

7. The method of claim 1 wherein the angle comprises a head-to-shoulder angle of a subject for the profile images.

8. An image analysis system for comparing a submental profile of a subject comprising:
   a camera for acquiring images of a subject, wherein the images comprise the submental profile of the subject when the subject's chin is tilted to vary head to shoulder angles for each of the images, further wherein the images comprise a variety of head to shoulder angles for a set of before images and for a set of after images;
   an image analyzer that compares the submental profile, the image analyzer comprising:
   a receiver that receives the images including before and after images of the submental profile for comparison;

a comparator for analyzing angles of the submental profile from the before and after images, wherein the comparator matches the head to shoulder angles of one image from the before images and of one image from the after images to establish pairs from the before images and the after images with a matching head to shoulder angle;

a generator for calculating an area of the submental profile for one of the pairs of the before and after images; and a differentiator for determining changes to a submental profile based on a comparison between the calculated area for pairs of images, wherein the changes comprise differences of the after images from the before images.

9. The image analysis system of claim 8 wherein the camera comprises a high speed camera capable of at least 15 images per second that takes the images while the subject moves his/her head in a vertical direction.

10. The image analysis system of claim 8 further comprising:

a chair including an adjustable height for maintaining a height of the subject for both the before images and the after images, wherein the chair includes an adjustable back that is moved vertically for positioning the subject at a similar location for both the before images and the after images.

11. The image analysis system of claim 10 wherein the chair includes a circular scale for controlling a direction in which the subject faces.

12. The image analysis system of claim 10 further comprising:

a booth coupled with the camera through which the images are acquired.

13. The image analysis system of claim 12 further comprising:

a connector that connects the chair and the booth, wherein the connector maintains a consistent distance between the camera and the subject for both the before images and the after images.

14. The image analysis system of claim 12 further comprising:

a horizontal slider coupled with the booth for adjusting the booth in a horizontal direction for maintaining a consistent distance between the camera and the subject for both the before and after images.

15. The image analysis system of claim 8 wherein the camera is connected with a vertical stand for adjusting a height of the camera relative to the subject.

16. The image analysis system of claim 8 wherein the calculating the area of the submental profile comprises identifying a tip of a tragus, a tip of a nose, a tip of a chin, and a base of a neck for each of the before and after images for a matched pair of images and calculating an area bounded by at least a portion of the identified tip of the tragus, tip of the nose, tip of the chin, and base of the neck.

17. The image analysis system of claim 16 wherein the area bounded comprises an area bounded by a first reference line tangent line from the nose that is normal to the tip of the tragus, a line from the base of the neck that is perpendicular to the first reference line; a line from the tip of the chin that is perpendicular to the first reference line.

18. The image analysis system of claim 17, wherein the differentiator compares calculated area after being normalized, further wherein the areas are normalized by dividing the area by a length of the first reference line.

19. A non-transitory computer readable storage medium having stored therein data representing instructions executable by a programmed processor for comparing facial profile images, the storage medium comprising instructions operative for:

receiving a plurality of first profile images taken while a head to shoulder angle is modified, wherein the first profile images comprise before images;

receiving a plurality of second profile images taken while a head to shoulder angle is modified, wherein the second profile images comprise after images;

determining an angle for each of the first and second profile images;

matching one of the before images with one of the after images based on the determined angle, wherein the matching comprises identifying multiple pairs of before and after images at different angles;

calculating a normalized area of the profile, including a submental area, for both of the matched before and after images; and identifying changes in the matched after image when compared with the matching before image.

20. The computer readable storage medium of claim 19 wherein the calculating the normalized area further comprises:

identifying a tip of a tragus, a tip of a nose, a tip of a chin, and a base of a neck for each of the before and after images for a matched pair of images; and calculating an area bounded by at least a portion of the identified tip of the tragus, tip of the nose, tip of the chin, and base of the neck.

21. The computer readable storage medium of claim 20 wherein the calculating the normalized area bounded further comprises:

identifying a first reference line that is a tangent line from the nose that is normal to the tip of the tragus;

identifying a second reference line that is a tangent line from the chin that is normal to the tip of the tragus;

identifying a third reference line from the base of the neck that is perpendicular to the first reference line;

identifying a fourth reference line from the tip of the chin that is perpendicular to the first reference line;

calculating an area bounded by the third reference line, the first reference line, the fourth reference line, and the neck; and normalizing the calculated areas of the profile for both of the matched before and after images, wherein the normalizing comprises dividing the calculated area by a length of the first reference line.

* * * * *